United States Patent
Verlaan et al.

(10) Patent No.: US 11,957,388 B2
(45) Date of Patent: *Apr. 16, 2024

(54) DEFORMABLE BODY AND COMBINATION OF SUCH DEFORMABLE BODY AND A SURGICAL SCREW ELEMENT

(71) Applicants: UMC UTRECHT HOLDING B.V., Utrecht (NL); BO-IP B.V., Zeist (NL)

(72) Inventors: Joannes Jacobus Verlaan, Zeist (NL); Bas Jeroen Oosterman, Zeist (NL)

(73) Assignees: UMC UTRECHT HOLDING B.V., Utrecht (NL); BO-IP B.V., Zeist (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,600

(22) Filed: Jan. 26, 2023

(65) Prior Publication Data

US 2023/0165605 A1  Jun. 1, 2023

Related U.S. Application Data

(63) Continuation of application No. 16/771,723, filed as application No. PCT/NL2018/050832 on Dec. 12, 2018, now Pat. No. 11,564,716.

(30) Foreign Application Priority Data

Dec. 12, 2017  (NL) ..................................... 2020071

(51) Int. Cl.
*A61B 17/58* (2006.01)
*A61B 17/70* (2006.01)
(Continued)

(52) U.S. Cl.
CPC ...... *A61B 17/7044* (2013.01); *A61B 17/7061* (2013.01); *A61L 27/20* (2013.01);
(Continued)

(58) Field of Classification Search
CPC ........................... A61B 17/044; A61B 17/7061
See application file for complete search history.

(56) References Cited

U.S. PATENT DOCUMENTS 8,333,791 B2  12/2012  Carls et al.
8,906,022 B2 * 12/2014  Krinke .................. A61B 17/68
606/63

(Continued)

FOREIGN PATENT DOCUMENTS

CN  101437571 A  5/2009
WO  2009/045743 A1  4/2009
(Continued)

OTHER PUBLICATIONS

International Search Report and Written Opinion for WO 2019/117715 (PCT/NL2018/050832), dated May 24, 2019, pp. 1-11.
(Continued)

*Primary Examiner* — Eyamindae C Jallow
(74) *Attorney, Agent, or Firm* — Thomas|Horstemeyer, LLP

(57) ABSTRACT

The present invention provides a deformable body (2), wherein the deformable body comprises a force application surface (12) opposite a bone contact surface (52) to be pressed against periosteum of a bone surface (52) of a bone such that the bone contact surface adapts its shape to the shape of the bone surface, wherein the deformable body comprises one or more through-going openings (3) and/or one or more fixation locations (34) arranged to receive a fixation element such as screw (20), and wherein the deformable body comprises an anaesthetic that is released from or through the bone contact surface. The anaesthetic can be bupivicaine, liposome bupivacaine, lidocaine or levobupivacaine. The anaestetic can be arranged in one or more compartments (6, 7) which have different release rates. The screw can comprise a detent or rim to mate with the
(Continued)

deformable body. A sleeve (80) can be arranged in the opening (3) to receive the screw. A pusher element (81) can push the deformable body from the sleeve into position on the screw shank (21).

21 Claims, 11 Drawing Sheets

(51) Int. Cl.
*A61L 27/20* (2006.01)
*A61L 27/22* (2006.01)
*A61L 27/52* (2006.01)
*A61M 31/00* (2006.01)
*A61B 17/00* (2006.01)
*A61B 17/56* (2006.01)

(52) U.S. Cl.
CPC ........... *A61L 27/222* (2013.01); *A61L 27/227* (2013.01); *A61L 27/52* (2013.01); *A61M 31/002* (2013.01); *A61B 2017/00004* (2013.01); *A61B 2017/00862* (2013.01); *A61B 2017/00889* (2013.01); *A61B 2017/00893* (2013.01); *A61B 2017/561* (2013.01)

(56) References Cited

U.S. PATENT DOCUMENTS

| | | | |
|---|---|---|---|
| 10,265,110 B2 * | 4/2019 | Williams | A61B 17/866 |
| 10,799,277 B2 * | 10/2020 | Kulper | A61B 17/7001 |
| 2004/0166140 A1 | 8/2004 | Santini, Jr. et al. | |
| 2008/0262630 A1 | 8/2008 | Fulmer et al. | |
| 2008/0317812 A1 | 12/2008 | Zhang et al. | |
| 2009/0048629 A1 * | 2/2009 | Rabiner | A61B 17/0401 604/509 |
| 2009/0131992 A1 * | 5/2009 | Greenhalgh | A61B 17/864 606/301 |
| 2010/0130959 A1 | 5/2010 | Boyd et al. | |
| 2010/0184685 A1 | 7/2010 | Zavala, Jr. et al. | |
| 2010/0217325 A1 * | 8/2010 | Hochschuler | A61B 17/864 606/86 R |
| 2012/0109222 A1 * | 5/2012 | Goel | A61B 17/8685 606/310 |
| 2013/0226251 A1 * | 8/2013 | Chegini | A61B 17/8625 606/325 |
| 2015/0201971 A1 * | 7/2015 | Gaines | A61B 17/7044 606/264 |
| 2019/0209215 A1 * | 7/2019 | Baynham | A61B 17/8042 |
| 2019/0290334 A1 * | 9/2019 | Prygoski | A61B 17/809 |
| 2020/0268517 A1 * | 8/2020 | Szalay | A61F 2/3094 |
| 2020/0375630 A1 * | 12/2020 | Kim | A61F 2/447 |

FOREIGN PATENT DOCUMENTS

| | | |
|---|---|---|
| WO | 2019/071243 A1 | 4/2019 |
| WO | 2019/071245 A1 | 4/2019 |
| WO | 2019/071246 A2 | 4/2019 |

OTHER PUBLICATIONS

UK Search Report for NL 2020071, dated Oct. 12, 2018, pp. 1-10.
Chinese Office Action for Patent Application No. 201880079720.8, dated Aug. 30, 2023, pp. 1-13 (Translation Included).

* cited by examiner

Figure 1
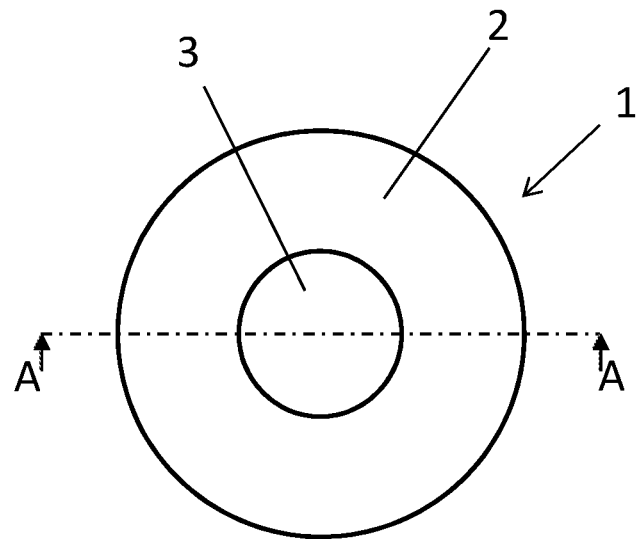
Figure 2 (A-A)
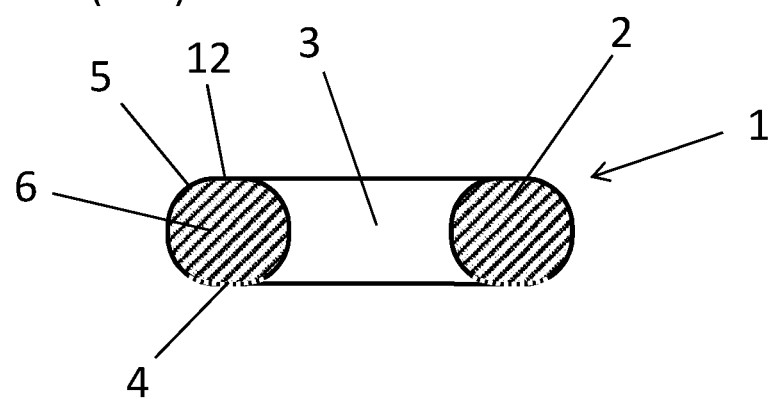

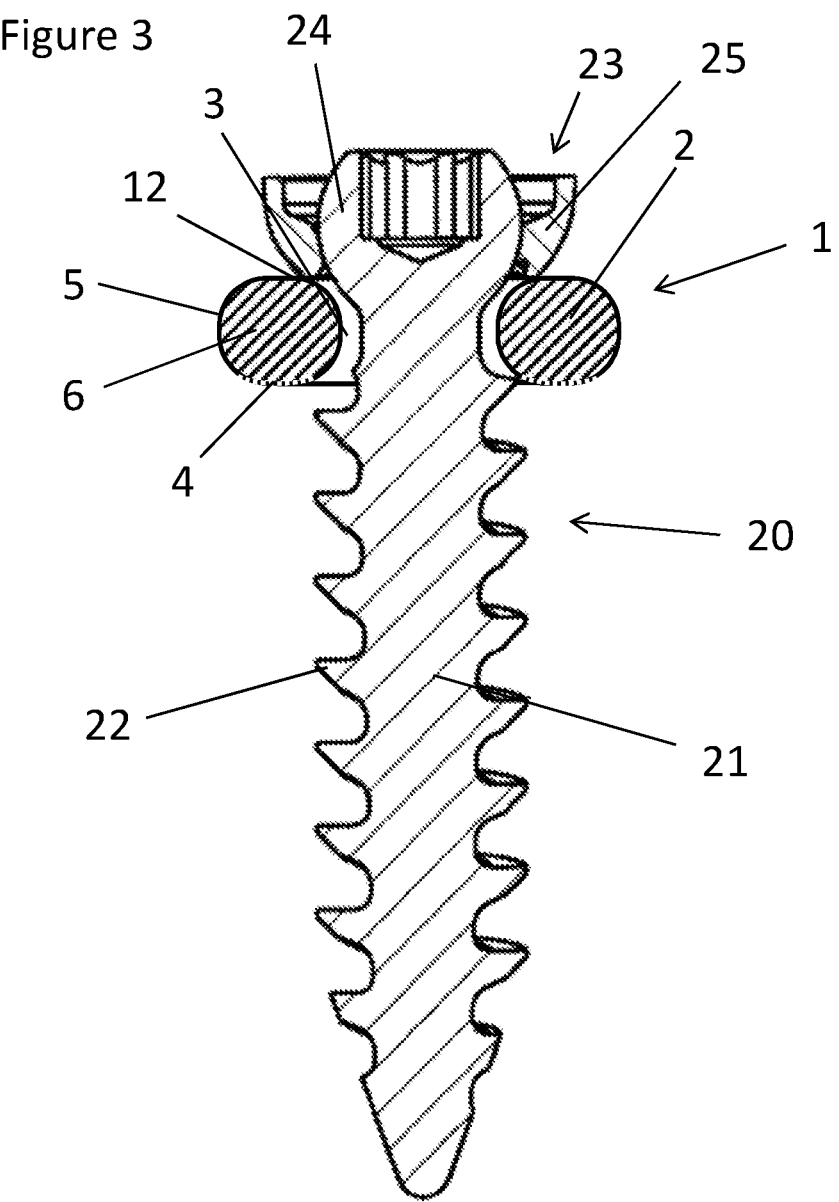

Figure 10
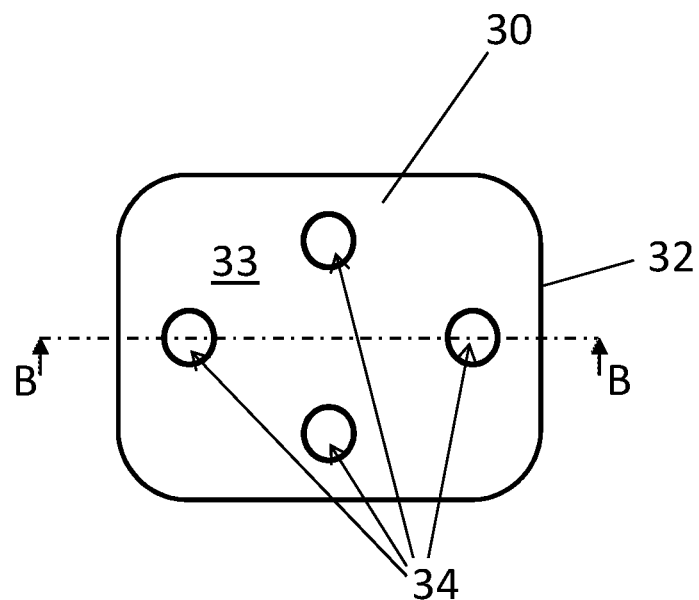
Figure 11 (B-B)
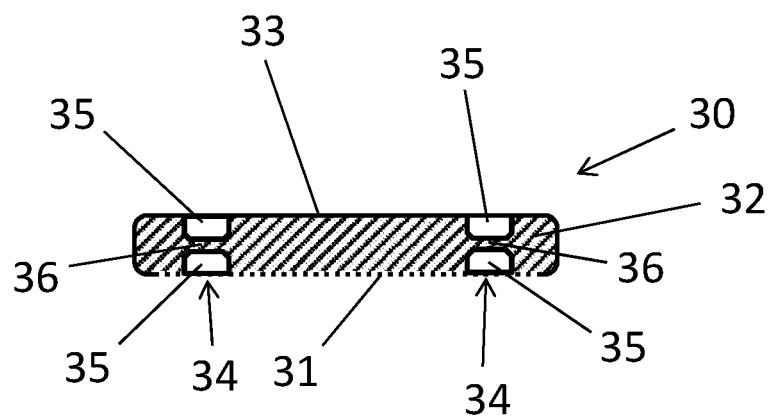

DEFORMABLE BODY AND COMBINATION OF SUCH DEFORMABLE BODY AND A SURGICAL SCREW ELEMENT

CROSS-REFERENCE TO RELATED APPLICATIONS

This application is a Continuation of U.S. patent application Ser. No. 16/771,723, filed Jun. 11, 2020, which is the National Stage of International Application No. PCT/NL2018/050832, filed Dec. 12, 2018, which claims priority to NL 2020071, filed Dec. 12, 2017, which are entirely incorporated herein by reference.

The present invention relates to a deformable body and to a combination of such deformable body and a surgical screw element.

US 2010/031228 discloses a pedicle screw system to be used in spinal fixation systems. In such spinal fixation system, pedicle screws are used to anchor the spinal fixation system in the respective vertebrae of the spine of the patient to be treated. The fixation of the spine may for example be used in treatment of diseased spines, for example caused by cancerous tissue or fractures being present in the spinal column of the patient.

For fixation of the spinal fixation system each of the pedicle screw elements is fixed through a respective pedicle of a vertebra of the patient. The placement of such pedicle screw element typically causes much pain, in particular due to the damage that is caused to the overlying periosteum of the vertebra as a result of the pedicle screw element being introduced in the pedicle of the vertebra.

To decrease the high level of pain experienced by the patient, high doses of analgesics, for example morphine, may be administered to the patient either through oral, subcutaneous, intramuscular or intravenous routes. However, in practice, the morphine doses necessary to provide a reasonable level of comfort to the patient often lead to relevant side-effects and/or adverse events.

It is an object of the invention to provide an improvement in the treatment of pain, in particular caused by placement of screw elements in the skeleton, whereby the periosteum is damaged by the screw elements. It is a further object of the invention to improve the treatment of pain in surgical procedures in which screw elements are placed in skeletal structures, for example pedicle screws introduced into the spine of a patient.

The present invention provides a deformable body as claimed in claim 1.

The deformable body of the present invention is an anaesthetic-carrying body intended to be pressed with its bone contact surface on the periosteum of an outer surface of a bone to be treated. By pressing the bone contact surface, also referred to as periosteum contact surface, of the deformable body on the periosteum, the deformable body will be deformed, preferably elastically deformed. As a result, the bone contact surface of the deformable body will adapt its shape to the shape of the outer bone surface, therewith covering the overlying periosteum of the bone.

In this application, deformable means that the material of the deformable body is flexible such that its surface shape can adapt to a shape of a surface against which the deformable body is pressed. The deformability of the deformable body is selected such that due to the deformation of the deformable body, the bone contact surface of the deformable body comes into intimate contact with the outer bone surface, when the deformable body is squeezed.

In practice, the deformability of the deformable body may be similar to the deformability of a wine gum.

In the deformable body an anaesthetic is provided which is released from or through the bone contact surface of the deformable body. When the bone contact surface of the deformable body is in intimate contact with the bone surface directly next to the location where the screw is brought into the bone, the anaesthetic is provided directly at the origin of the pain, in particular due to the damaged periosteum, experienced by the patient. This results in an effective pain relief for a patient that is treated. Since the anaesthetic is released directly at the desired location, less anaesthetic will have effect in tissue in the surrounding area, i.e. in areas where less pain relief by anaesthetics is desired.

The Young's modulus of the material of the deformable body may be in the range of 1 kPa-1 GPa, for example in the range of 10 kPa-1 GPa. The yield point of the material of the deformable body may be in the range of 10 Pa-20 MPa.

The material of the deformable body may be soft material, for example substantially softer than metals.

The deformable body comprises one or more through-going openings and/or one or more fixation locations, arranged to receive a fixation element therethrough. It is of importance that the bone contact surface of the deformable body is pressed against the bone surface of a bone to be treated. The deformable body may be provided with one or more through-going openings to accommodate a fixation element, for example a screw element, that can be used to fix the deformable body on the bone and/or to press the deformable body against the bone surface. The one or more through-going openings may also be used to arrange other fixation elements therethrough, such as, when used in combination with, for example, a plate, a wire or a band.

In an alternative embodiment, the deformable body may comprise one or more fixation locations that are arranged to receive a fixation element therethrough. The one or more fixation location may be grooves or recesses that allow the fixation element to hold the deformable body at a desired location on a bone surface, and to press the deformable body on the bone surface.

In an embodiment, the deformable body may have two recesses at opposite sides of the deformable body, such that a thin part, for example a membrane, remains between the two recesses. This thin part may be pierced by for example a screw element to form a through-going opening. The thin part may also be created by arranging a recess at one side of the deformable body.

The administration of the anaesthetic can be modulated to provide a desirable release profile of the anaesthetic over time.

The anaesthetic may be an amino-amide local anesthetic, such as lidocaine, prilocaine, bupivicaine, levobupivacaine, ropivacaine, mepivacaine, lidocaine, dibucaine, etidocaine, or other amino-caine. The anaesthetic may also comprise a combination of two or more types of anaesthetics. Preferably, the anaesthetic is bupivicaine, liposome bupivacaine or levobupivacaine, lidocaine, or a combination of anaesthetics comprising bupivicaine, liposome bupivacaine and/or levobupivacaine.

It is remarked that U.S. Pat. No. 8,333,791 discloses the use of ties that can be coupled on with one or more parts of a medical device after the medical device has been implanted in the human body. The medical device is for example a pedicle screw or spinal rod around which the tie may be provided. The tie has a time-release therapeutic substance incorporated therein. After the surgical procedure is completed the tie will release the therapeutic substance when the tie is exposed to an at least in part aqueous substance.

Further, WO 2009/045743 discloses the use of non-load bearing spinal components comprising a pharmaceutical component in a spinal screw assembly. The non-load bearing spinal component is for example bone screw cap mounted on the proximal end of a screw element of the spinal screw assembly. In another embodiment, the non-load bearing spinal component is provided as a rod cover configured to be arranged on a spinal rod of the spinal screw assembly. After implantation, the pharmaceutical component is released from the non-load bearing spinal component according to a desired release profile.

The deformable body of the present invention uses a different approach compared to the devices of U.S. 8,333,791 and WO 2009/045743. The devices of U.S. 8,333,791 and WO 2009/045743 are configured to release pharmaceutical compounds in a surrounding area, while mounted on a spinal screw assembly. The deformable body of the present invention is pressed with its bone contact surface against the periosteum, whereby the shape of the bone contact surface is adapted to the actual surface profile of the bone surface of the periosteum. The anaesthetic present in the deformable body, and released from or through the bone contact surface is directly administered at the desired location, i.e. the punctured periosteum which typically is the origin of intense pain experienced by the patient. As a result, pain can be treated more directly and effectively. Furthermore, no or little anaesthetic will unintentionally diffuse into and/or have effect on tissue including the spinal cord, nerve roots and peripheral nerves in the near-field area.

Thereby, it is remarked that the devices of U.S. 8,333,791 and WO 2009/045743 are not typically configured to treat pain, and therefore the location of these devices is of less importance compared to the specific pain treatment objective of the deformable body of the present invention.

The deformable body of the invention may be applied in the living human and/or animal body.

In an embodiment, the deformable body comprises a force application surface to apply a force on the deformable body to press the bone contact surface on the periosteum of a bone to be treated. The bone contact surface may be arranged at a first side of the deformable body and force application surface may be arranged at a second side of the deformable body, wherein the first side and the second side are opposite sides of the deformable body.

In an embodiment, the body may be bio-absorbable and/or biodegradable.

In an embodiment, the deformable body is a deformable ring-shaped body having an opening. This opening is one of the one or more through-going openings, for example a central opening in the ring-shaped body. The size of the opening has been selected such that the shank of a surgical screw element can be arranged through the ring-shaped body. The screw element typically comprises a proximal part, for example a screw head, which has an increased diameter compared with the shank of the screw element. The diameter of the opening of the deformable body may be selected to be smaller than the diameter of the proximal part of the screw element. The screw element may be a complete screw or a part thereof. The screw element at least comprises a shank with screw thread and a proximal part having a larger diameter than the shank diameter.

The ring-shaped body may be arranged on the shank of the screw element before the screw is screwed into a bone structure, for example a pedicle of a vertebra. When the screw element carrying the ring is screwed into a bone, the ring-shaped body will be squeezed between the bone surface and the proximal part of the screw element. Due to this squeezing the deformable ring-shaped body will be deformed, preferably elastically deformed, between the bone surface and the proximal part of the screw element. As a result, the bone contact surface of the ring-shaped body will be firmly pressed against the bone surface, while the bone contact surface adapts its shape to the shape of the bone surface.

The ring-shaped body may have any shape having an opening through which the shank of a screw element may extend. The outer surface of the ring extending around the opening may be circular, but also oval, polygonal, such as triangular, square, pentagonal with respect to a longitudinal axis of the opening. The cross section of ring may also be of any suitable shape, such as circular, oval, and polygonal. In an embodiment, the ring-shaped element has a donut like shape.

It is remarked that in an alternative embodiment, the deformable body may be a disc shaped body having a central thin part, for example a membrane, or, conversely, a protruding part that can be pierced by a screw element to form an opening.

In an embodiment, the deformable body comprises a holding element or holding means, such as a lip, rim, bulge, or clip to hold the deformable body on the shank of a screw element and/or to connect the deformable body with a plate element, in an aligned position with a plate opening in the plate element. In an alternative embodiment, the deformable body may be glued on a plate element in an aligned position with the plate opening.

In an embodiment, the deformable body may have any shape suitable to be implanted at a desired location.

In an embodiment, the bone contact surface is pervious for the anaesthetic to be released. For example, the bone contact surface is a porous or permeable surface through which the anaesthetic is released. The bone contact surface may become pervious for the anaesthetic after a predetermined time after implantation of the deformable body. For example, the bone contact surface may have a water-soluble coating or a coating that dissolves when heated at body temperature.

The anaesthetic may be provided in the deformable body, for example as particles provided with a coating that may dissolve in an aqueous solution. When the bone contact surface is a pervious surface for the anaesthetic, the anaesthetic may leave the deformable body through the bone contact surface. Since the bone contact surface is intended to be firmly pressed against the bone surface, the anaesthetic will directly be released on the bone surface.

In an embodiment, the anaesthetic is arranged in a compartment delimited by the bone contact surface and a further compartment wall, wherein the further compartment wall is a substantially non-pervious wall such that anaesthetic will mainly be released through the bone contact surface.

The anaesthetic may be held in a compartment that is delimited by the bone contact surface and the further compartment wall, whereby the further compartment wall is a substantially non-pervious wall for the anaesthetic, i.e. the further compartment wall does not allow the anaesthetic to pass the further compartment wall or allows substantially less anaesthetic to pass the further compartment wall in comparison with anaesthetic that passes during a same time period through the bone contact surface. As a result, the anaesthetic will mainly be released from the deformable body through the bone contact surface. This further ensures that the anaesthetic is directly released on the bone surface next to the location where the screw element is brought through the periosteum of the bone.

Since the anaesthetic is mainly released directly at the desired location, less anaesthetic will have effect in tissue in the surrounding area, i.e. in areas where no pain relief by anaesthetics is desired. Also, since substantially all anaesthetic is used at the location of interest, no additional anaesthetic has to be released in order to compensate anaesthetic that will not be used at the desired location of treatment. It is remarked that some pain relief may be desired in the damaged skin and muscles, but this can be achieved with regular, low dose painkillers.

Although the deformable body is designed for release at a specific side of the compartment of the deformable body, for example at the bone contact surface, the characteristics of the compartment walls, such as the bone contact surface and the further compartment wall may, after implantation, change over time due to degradation of the deformable body, for example since the deformable body is biodegradable or bioabsorbable. This means that the difference in perviousness of the bone contact surface and the further compartment wall may substantially change over time, after implantation, due to degradation of the deformable body.

In an embodiment, the bone contact surface has a first permeability for the anaesthetic to be released and wherein the further compartment wall has a second permeability for the anaesthetic to be released, wherein the first permeability is larger than the second permeability. In an embodiment, the further compartment wall may be impermeable for the anaesthetic to be released In an embodiment, the anaesthetic is arranged in a compartment delimited by the bone contact surface and a further compartment wall, wherein the bone contact surface has a first release rate for the anaesthetic to be released and wherein the further compartment wall has a second release rate for the anaesthetic to be released, wherein the first release rate is larger than the second release rate. The first release rate and second release rate are defined as the quantities of anaesthetic that are released per $cm^2$ surface area, during a same period, through the bone contact surface and through the further compartment wall, respectively.

Preferably, the first release rate is at least 2 times larger than the second release rate, more preferably at least 5 times larger than the second release rate, even more preferably at least 10 times larger than the second release rate.

The further compartment wall may be formed by the same material as the inner side of the compartment, but may for example be specifically treated, for example by cross linking to adapt the release properties of the further compartment wall.

The further compartment wall may also be provided by a layer provided on or in the deformable body, for example a coating which is substantially impermeable for the anaesthetic.

In an embodiment, the further compartment wall is an outer wall of the deformable body. In this embodiment, the complete deformable body forms a compartment delimited by an outer wall of the deformable body. From this compartment, only or at least mainly the bone contact surface will allow the release of anaesthetic from the deformable body. The further outer wall of the deformable body is preferably made non-pervious, for example impermeable for the anaesthetic.

In an embodiment, both mechanical robustness and directional release may be provided by an external shell arranged at least partially on the deformable body. This shell can be constructed from the same material as the anaesthetic containing interior of the deformable body of the device with altered mechanical and chemical properties, for example more dense crosslinking, or an alternative method of crosslinking. Alternatively, the shell can be constructed from a different polymer, for example a synthetic polymer such as polylactic-co-glycolic acid (PLGA), polycaprolactone (PCL) or polyvinyl alcohol (PVA), or a biopolymer such as hyaluronic acid, chitosan, alginate, collagen or gelatin. These polymers can be functionalized with a variety of chemical groups to modulate their characteristics.

The external shell may provide a robust housing for the anaesthetic-containing interior of the deformable body and may bear most of the mechanical strain/load during insertion of the deformable body. As the permeability and porosity of the shell can be adjusted, the release can be directed towards a desired location, i.e. the bone contact surface. This contact surface, with which the deformable body is arranged on the periosteum, may not be covered with the external shell to provide an opportunity for diffusion of the anaesthetic and degradation of the interior of the deformable body. In an alternative embodiment, the side of the deformable body comprising the bone contact surface may also be covered with the external shell but this part of the shell may have an increased porosity and permeability for the anaesthetic compared to the other parts of the external shell. This can for example be achieved with macroscopic or microscopic pores. To control the ratio between anaesthetic diffusion towards the bone contact surface and diffusion towards the other surfaces, the porosity of the part of the shell that encapsulates the other surfaces of the device can be adjusted with either microscopic and/or macroscopic pores or other means to alter permeability.

The shell is flexible to adapt its shape to the bone surface on which it is pressed. The shell may be biodegradable, with the degradation time for example being similar or slightly surpassing the degradation time of the drug-containing interior of the deformable body.

In an embodiment, the deformable body comprises a second compartment at least partially delimited by a release surface, wherein the second compartment comprises a second pharmaceutical or biological compound, and wherein the release surface is pervious for the second pharmaceutical or biological compound. In this embodiment, the deformable body comprises two compartments, for example separated by a substantially non-pervious separation wall provided between the first compartment and the second compartment.

As described above, the first compartment comprises an anaesthetic that may be released through the bone contact surface directly on the bone surface, where treatment of pain is desired. The second compartment may comprise a second pharmaceutical or biological compound that may be released through the release surface pervious for the second pharmaceutical or biological compound. The pervious release surface of the second compartment may be arranged in such way as to not be pressed against the bone surface, when the deformable body is squeezed between the bone surface and the proximal part of the screw element. The second pharmaceutical or biological compound will therefore be released at a distance from the bone surface, and be further distributed within the area in which the screw element is placed. The second compartment may for example be used to release antibiotics or analgesics in the surrounding soft-tissue area of the bone-screw assembly.

Additionally, or alternatively, the deformable body may comprise a further compartment at least partially delimited by a further release surface, wherein the further compartment comprises a further pharmaceutical or biological compound, and wherein the further release surface is pervious for the further pharmaceutical or biological compound, wherein the release surface is arranged to be pressed together with the bone contact surface against a periosteum of an outer bone surface of a bone to be treated. In this embodiment, the deformable body can be used to release in addition to the anaesthetic, a further pharmaceutical or biological compound directly on the periosteum of an outer bone surface on which the deformable body is pressed. The further pharmaceutical or biological compound is for example a bone cancer drug or a regenerative drug.

The advantage of such further compartment is that the release profile of the anaesthetic and the release profile of the further pharmaceutical or biological compound can each be optimized for the anaesthetic and the respective pharmaceutical or biological compound.

In an alternative embodiment, a further pharmaceutical or biological compound may be provided in the same material/compartment as the anaesthetic, such that the further pharmaceutical or biological compound may be released together with the bone contact surface through or from the bone contact surface.

In an embodiment, a side of the deformable body comprising the bone contact surface is flattened. To improve the contact surface between the bone contact surface and a relatively flat bone surface, the bone contact surface may be provided as a flattened surface, when compared to a more circular cross-section.

In an alternative embodiment, the shape of the bone contact surface, in non-deformed state, may be adapted to a typical shape of a bone surface against which the deformable body will be pressed during use. This allows the bone contact surface to be more easily be brought into intimate contact with the bone surface to be treated.

In an embodiment, the deformable body comprises one or more deformation indicators that indicate a deformation, in particular a degree of deformation of the deformable body. In order to obtain, during use, an intimate contact between the bone contact surface and the bone surface, it is of importance that the deformable body is properly pressed against the bone surface so that the deformable body is deformed to adapt the shape of the bone contact surface to the shape of the bone surface on which it is placed. To confirm that the deformable body is sufficiently deformed, the deformable body is provided with one or more deformation indicators that indicate a degree of deformation of the element.

The one or more deformation indicators may for example comprise one or more markers that move upon deformation of the deformable body, wherein this movement is detectable by a user.

In a ring-shaped embodiment of the deformable body, the one or more deformation indicators may comprise one or more markers that are arranged to move outwards in a radial direction upon deformation of the deformable body. The one or more markers may be arranged at one or more locations which are, when the deformable body is arranged on the shank of the screw element, seen in longitudinal/axial direction of the screw element concealed behind the proximal part of the screw element. Upon deformation of the deformable body, when being squeezed between the proximal part of the screw element and the bone surface, the one or more markers may move in radial direction to a location where the one or more markers are no longer concealed behind the proximal part of the screw element, when seen in longitudinal/axial direction of the screw element. Thus, when the one or more markers are visible, it can be concluded that the deformable body has been substantially deformed, and as a consequence, the bone contact surface is sufficiently pressed against the bone surface.

In an embodiment, the deformable body is at least partially radiopaque and/or the deformable body comprises one or more radiopaque elements. To make the deformable body at least partially radiopaque, the outer wall or shell of the deformable body may be impregnated with a radiopaque material or a radiopaque coating may be provided over at least a part of the outer surface of the deformable body. The one or more radiopaque elements may for example be particles that are arranged on the outer surface of deformable body and/or at least partially embedded in the deformable body. The one or more radiopaque elements facilitate the detectability of the deformable body using fluoroscopy, X-ray or CT techniques.

In addition, or as an alternative, the deformable body comprises materials that can be visualized by ultrasound techniques.

In an embodiment, the deformable body comprises one or more markings indicating a location of the bone contact surface. In order for the deformable body to be used properly, a marking may be provided that indicates directly or indirectly the location of the bone contact surface such that it can easily be checked that the bone contact surface is arranged or will be arranged against the bone surface.

The marking may for example be a line, sign and/or colour indicating the location of the bone contact surface, but may also be a marking that indicates the orientation with which the deformable body should be arranged on a bone surface. It will be clear that the latter marking also indirectly indicates the location of the bone contact surface.

It is remarked that other markings may be provided to indicate other relevant details of the deformable body, for example one or more of an anaesthetic dose, an anaesthetic release profile, a size, a dose of second pharmaceutical or biological compound, a second or biological pharmaceutical compound release profile, etc.

In an embodiment, the deformable body is made of a visco-elastic material, a degradable felt material, a sponge-like material, a gelatin material, a gel, in particular a hydrogel, a polymer or any combination thereof. The deformable body may be made of any suitable material that provides a suitable deformation of the deformable body due to pressing the deformable body on the periosteum of an outer bone surface, for example by squeezing the deformable body between a proximal part of a screw element and the bone surface of the bone in which the screw element is screwed.

Other examples of suitable material to form the deformable body are polylactic-co-glycolic acid (PLGA), polycaprolactone (PCL), alginates, polymers, etc.

Since the deformable body is intended to be implanted in a living human or animal body, the materials of the deformable body are preferably biocompatible and/or biodegradable materials. The degradation of the material(s) of the deformable body may be in the range of 3 days-26 weeks after implantation.

In an embodiment, the deformable body is freeze-dried. Freeze-drying the deformable body may substantially increase the shelf-life of the deformable body. Freeze-drying may also improve mechanical properties of the deformable body.

The invention also relates to a combination of the deformable body of any of the claims 1-15 and a surgical screw element having a shank, wherein the deformable body is arranged on the shank of the surgical screw element.

The deformable body may for example be a ring-shaped element having an opening, for example a central opening. The diameter of the opening of the ring-shaped element may substantially correspond to the diameter of the shank of the surgical screw element. The diameter of the opening may be slightly larger than the shank diameter so that the ring-shaped element can easily be placed on the shank of the screw element. The diameter of the opening may however also be slightly smaller than the shank diameter so that the ring-shaped element will clamp on the shank due to the deformation required to fit the ring-shaped element on the shank of the screw element.

A holding element, such as a lip, rim, clip, screw thread etc. may be used to hold the deformable body on the shank of the screw element. The holding element may be provided on the screw element and/or on the deformable body.

The screw element further comprises a proximal part having a diameter which is larger than the diameter of the opening of the ring-shaped element, for example a screw head or a connector, for instance to connect further parts of a spinal fixation system. The proximal part may be any part that is arranged proximal of the location of the ring-shaped element on the shank of the screw element and has a diameter which is larger than the diameter of the opening of the ring-shaped element. The proximal part may be integrally provided with the screw element, or may be a separate part of the screw element, or a combination thereof. The proximal part may also specifically be provided to squeeze the ring-shaped element between the proximal part and the bone surface.

The screw element may be a standard screw element, i.e. not specifically adapted for use in combination with the ring-shaped element. The ring-shaped element may be specifically designed to fit on the shank of the standard screw element, or possibly a range of standard screw elements.

In an alternative embodiment, the screw element may be specifically adapted to be provided together with the ring-shaped element. For example, the shank of the screw element may be adapted to receive the ring-shaped element. In such embodiment, the shank of the screw element may comprise a circumferential rim or circumferential detention that mates with the ring-shaped element in order to hold the ring-shaped element on the shank of the screw element.

The present invention further relates to bupivicaine, liposome bupivacaine, lidocaine or levobupivacaine for use in a method of treating pain, in particular pain caused by placing a surgical screw element through periosteum of a bone of a patient,
wherein the bupivicaine, liposome bupivacaine, lidocaine or levobupivacaine is administered by a deformable body as claimed in any of the claims 1-19.

The present invention furthermore relates to a method of treating pain, in particular pain caused by placing a surgical screw element through periosteum of a bone of a patient, comprising the steps of:
placing a deformable body on a shank of the surgical screw element, wherein the deformable body comprises a bone contact surface to be pressed against bone surface upon screwing of the screw element in a bone, and wherein the deformable body comprises an anaesthetic that is released from or through the bone contact surface.
screwing the surgical screw element into the bone of the patient, whereby the deformable body is squeezed between the bone surface and a proximal part of the screw element to press the bone contact surface against bone surface, and
releasing the anaesthetic from or through the bone contact surface.

It is remarked that according to the present invention, the deformable body comprises an anaesthetic. In alternative embodiments, the deformable body may comprise, in addition to or as an alternative, other pharmaceutical or biological compounds.

The term "pharmaceutical or biological compound", as used herein, refers to any substance used internally as a medicine/drug for the treatment, cure, or prevention of a disease or disorder. Examples of pharmaceutical or biological compounds that can be administered using the deformable body of the present invention are for example anaesthetics, antibiotics, bone growth stimulating agents, analgesics, chemotherapeutic agents, steroids (including retinoids), hormones, anti-microbials, antivirals, anti-inflammatory compounds, radiation absorbers, including UV-absorbers, vaccins, and stemcells.

The active pharmaceutical compound is included in the composition in an amount sufficient to deliver to the host patient an effective amount to achieve a desired effect. The amount of drug or biologically active agent incorporated into the composition depends upon the desired release profile, the concentration of drug required for a biological effect, and the desired period of release of the drug.

Embodiments of the invention will now be described, by way of example only, with reference to the accompanying schematic drawings in which corresponding reference symbols indicate corresponding parts, and in which:

FIG. 1 shows a top view of a ring-shaped element according to an embodiment of the invention;

FIG. 2 shows a cross-section A-A of the ring-shaped element of FIG. 1;

FIG. 3 shows a combination of a screw element and the ring-shaped element of FIG. 1 arranged on the shank of the screw element;

FIG. 10 shows an alternative embodiment of a deformable body according to the invention;

FIG. 11 shows a cross-section B-B of the deformable body of FIG. 10;

Figure 4:
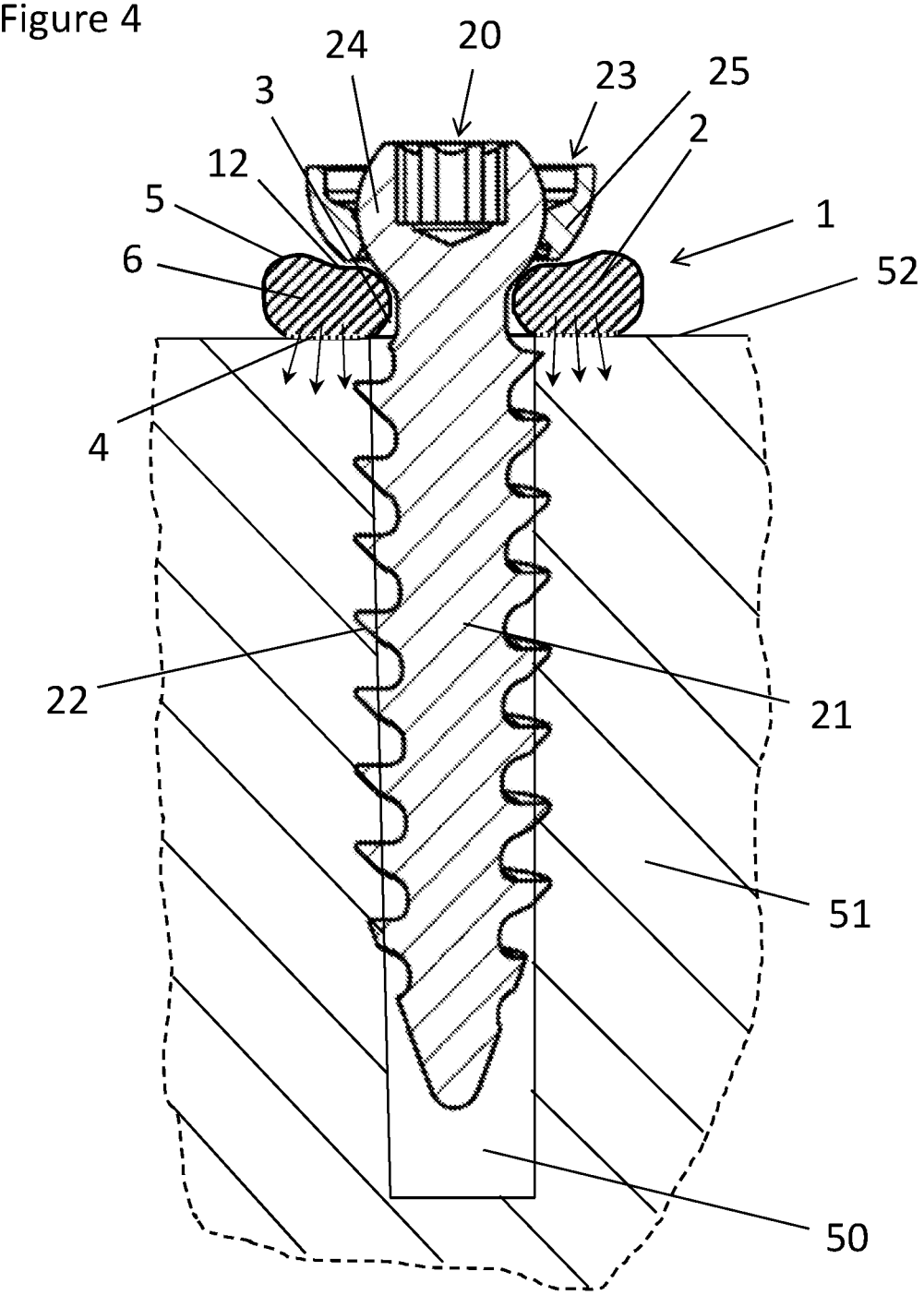
FIG. 4 shows the combination of FIG. 3 screwed into a bone of a patient.

FIG. 1 shows a top view of a deformable body according to an embodiment of the invention in the form of a ring-shaped element, generally denoted by reference numeral 1. The ring-shaped element 1 comprises a deformable ring body 2 having a central opening 3. The ring-shaped element 1 is designed to be placed on a shank of a surgical screw element, for example a pedicle screw of a spinal fixation system.

The ring body 2 is made of a deformable biocompatible material, for example gelatin material. The ring-shaped element 1 is preferably bio-absorbable.

FIG. 2 shows a cross-section A-A of the ring-shaped element 1. The outer surface wall of the ring-shaped element 1 is formed by a bone contact surface 4 and a compartment wall 5. The bone contact surface 4 and the compartment wall 5 delimit a compartment 6. The compartment 6, basically formed by the ring body 2 contains bupivacaine. The bone contact surface 4 is provided to be pressed on the periosteum of a bone to be treated. The bone contact surface 4 has, after implantation, a first release rate for the anaesthetic to be released and the compartment wall 5 has a second release rate for the anaesthetic to be released. The first release rate is substantially larger than the second release rate, for example at least 2, preferably at least 10 times the second release rate. As a result, the bupivacaine will be released from the compartment 6 mainly through the bone contact surface 4 according to a desired release profile over time.

The bone contact surface 4 to be pressed on the periosteum of a bone is arranged at a first side of the ring-shaped element. At a second side of the ring-shaped element 1, opposite to the first side, a force application surface 12 is provided. The force application surface 12 is arranged to apply a force on the ring-shaped element 12 to press the ring-shaped element 12 on the periosteum.

FIG. 3 shows a combination of a surgical screw element 20 and the ring-shaped element 1 of FIG. 1 mounted on a shank 21 of the screw element 20. The shank 21 comprises a screw thread 22 to screw the screw element 20 into bore provided in a bone of a patient. The screw element 20 further comprises a proximal part 23 having a screw head 24 integral with the shank 21 and a separate connector part 25. It is remarked that the screw element 20 is a standard screw element, i.e. not specifically adapted for use in combination with the ring-shaped element 1. The screw element 20 is for example a screw element of the spinal fixation system disclosed in US 2010/031228.

The diameter of the central opening 3 of the ring-shaped element 1 substantially corresponds to the diameter of the shank 21, such that the shank 21 can be moved through the ring-shaped element 1 to the position shown in FIG. 3. In this position of the ring-shaped element 1, the ring-shaped element 1 cannot be moved further in the proximal direction of the shank 21 as the proximal part 23 of the screw element 20 prevents such movement, since the diameter of the proximal part 23 is substantially larger than the diameter of the central opening 3.

The outer diameter of the ring-shaped element 1 may, for example, be in the range of 1 mm to 40 mm, preferably in the range of 5 mm to 25 mm. The diameter of the central opening 3 may for example be in the range 0.25 mm to 20 mm, preferably in the range of 2 mm to 15 mm.

FIG. 4 shows the combination of the surgical screw element 20 and the ring-shaped element 1 after it has been screwed into a bore 50 provided in a bone 51 of a patient to be treated. The bone 51 is for example a pedicle of a spine of a patient.

It can be seen that the ring-shaped element 1 is squeezed between the proximal part 23 of the screw element 20 and bone surface 52 of the bone 51. As a result of this squeezing, the ring body 2 is deformed resulting in an intimate contact between the bone contact surface 4 and the bone surface 52. Due to this intimate contact, the bupivacaine that is released from the compartment 6 through the bone contact surface 4 (as indicated by arrows) will be directly administered to the periosteum which is damaged due to the introduction of the screw element 20. Thus, the ring-shaped element 1 allows to directly administer locally a pharmaceutical compound, in particular bupivacaine to relief the pain that the patient experiences due to the damage of the periosteum. Since the compartment wall 5 of the ring-shaped element 1 has a relatively low permeability for the bupivacaine, the bupivacaine will mainly be released through the bone contact surface which is in direct contact with the bone to be treated. This allows for a very specific local delivery of the bupivacaine, which is generally desirable. Also, since the bupivacaine is released directly at this specific location, no or little bupivacaine will be spilled in tissue in the surrounding area, i.e. in areas where no pain relief is desired. This allows for administration of a more precise amount of bupivacaine during a predetermined timeperiod and at the desired location and also prevents side effects of the release of bupivacaine.

The deformability of the ring body 2 is designed such that the shape of the bone contact surface 4 adapts to the bone surface 52 on which it is pressed. This means that the bone contact surface 4 will follow irregularities of the bone surface. In practice, the consistency and deformability of the ring body 2 may be similar to a wine gum.

The bone contact surface 4 of the ring-shaped element 1 shown in FIGS. 1-4 is relatively flat and therefore in particular suitable for bone surfaces that are mainly flat. Generally, it is possible to adapt the shape of the deformable body and its bone contact surface 4 to other typical shapes of skeletal bones and implants at the location where screw elements are introduced into the bone in accordance with typical surgical procedures including, but not limited to, (plate—) fixation of: long bones, the pelvis, ribs, the shoulder girdle, large joints of the hip and knee and ankle, elbow, wrist, hand and foot, dental implants and cranial/maxillar/mandibular osteosynthesis instrumentations.

The bupivacaine is released according to a desired release profile over time.

Figure 5:
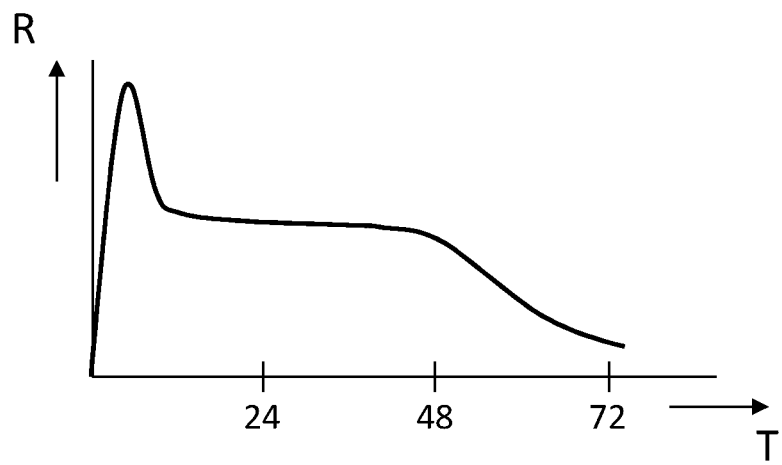
FIG. 5 shows an example of a release profile of the ring-shaped element of FIG. 1.

FIG. 5 shows an example of such release profile. In FIG. 5, the horizontal axis indicates time T in hours and the vertical axis indicates the amount of bupivacaine R that is released from the ring-shaped element 1 through the bone contact surface 4.

Directly after implantation of the screw element 20 a high level of pain is experienced by a patient in which the screw element is placed 20. To counteract this pain a peak of bupivacaine release is realized as quickly as possible in the first twelve hours after implantation. Thereafter, the bupivacaine release is maintained at a desired level until approximately 48-72 hours after implantation. Thereafter, the bupivacaine release may slowly decrease to zero.

Any other desirable release profile may also be designed using bupivacaine or another anaesthetic or combination of anaesthetics.

Figure 6:
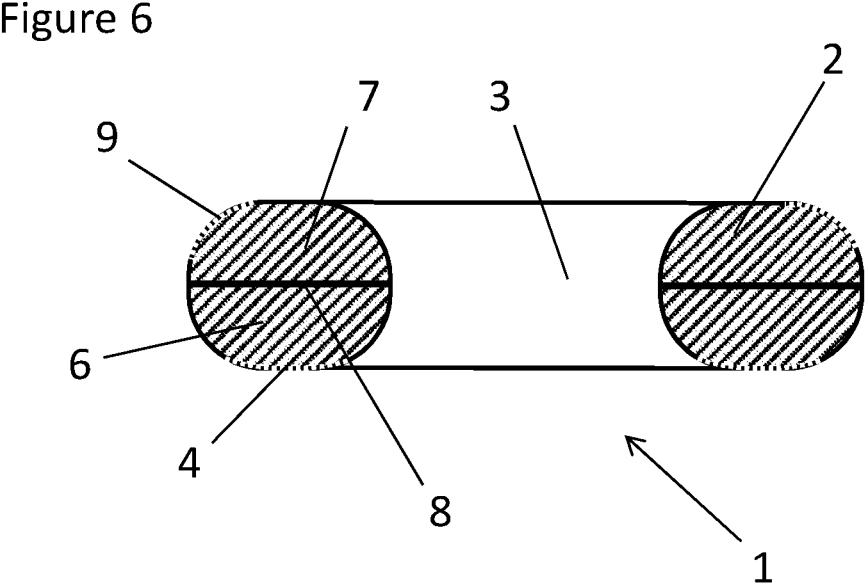
FIG. 6 shows a first alternative embodiment of a ring-shaped element according to the invention.

FIG. 6 shows a first alternative embodiment of a ring-shaped element 1 according to the invention. In the ring-shaped element 1 of FIG. 6 a first compartment 6 containing bupivacaine and a second compartment 7 containing a second pharmaceutical compound, for example antibiotics, are provided. The first compartment 6 and the second compartment 7 are separated from each other by a separation wall 8.

The first compartment 6 is partly delimited by the bone contact surface 4 that will be pressed during use against a bone surface 52 to be treated. The bone contact surface has a relatively high permeability for bupivacaine. The other walls delimiting the first compartment 6 have a relatively low permeability for bupivacaine, i.e. do not allow bupivacaine to pass the respective walls, or only allow a relatively low quantity of bupivacaine to pass the respective walls.

The second compartment is partly delimited by a release surface 9 having a relatively high permeability for the second pharmaceutical compound. The other walls delimiting the second compartment 6 have a relatively low permeability for the second pharmaceutical compound, i.e. do not allow the second pharmaceutical compound contained in the second compartment 7 to pass through these other walls, or only allow a relatively low quantity of the second pharmaceutical compound to pass through these other walls.

The release surface 9 will typically not be pressed against the bone surface 52, when the ring-shaped element 1 is squeezed between the bone surface 52 and the proximal part 23 of the screw element 20. As a result, the second pharmaceutical compound will be released at a location spaced from the bone surface 52, and the second pharmaceutical compound will be more distributed over the area in which the screw element is placed. The second compartment 7 of the ring-shaped element 1 may therefore typically be used to create such locally more distributed release of a pharmaceutical compound, for example antibiotics.

Figure 7:
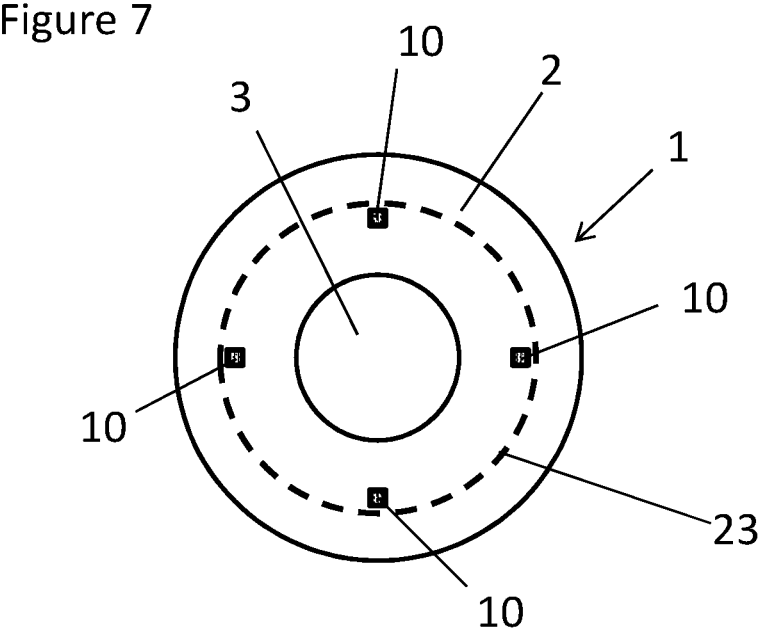
FIGS. 7 and 8 show a second alternative embodiment of a ring-shaped element according to the invention.
Figure 8:
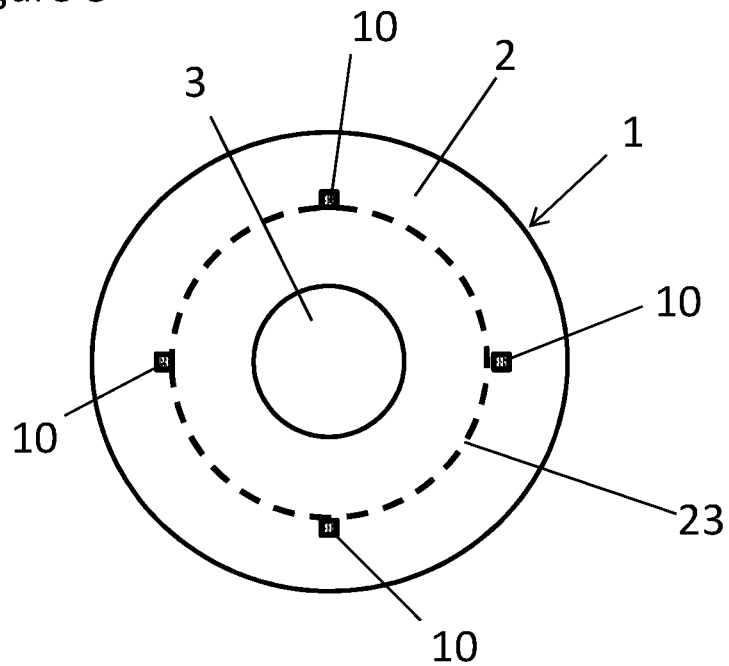

FIG. 7 shows a second alternative embodiment of a ring-shaped element 1. The ring-shaped element 1 of FIG. 7 comprises four deformation indicators, in the form of four markers 10 that indicate a degree of deformation of the ring-shaped element 1. The four markers 10 are arranged on a top surface of the ring-shaped element 1 distributed over the circumference of the ring-shaped element 1. When seen in longitudinal direction of a screw element 20 arranged through the ring-shaped element 1 the four markers are concealed behind the proximal part 23 (shown in dashed line) of the screw element 20.

To obtain an intimate contact between the bone contact surface 4 and the bone surface 52, the ring body 2 is deformed to adapt the shape of the bone contact surface 4 to the bone surface 52 on which it is placed.

The markers 10 are each arranged at a respective location that moves radially outwards when the ring body 2 is deformed due to squeezing between the bone surface 52 and the proximal part 23 of the screw element 20. As a result of this radially outwards movement of the markers 10 when the ring body is deformed, the markers 10 are no longer concealed by the proximal part 23 of the screw element 20 as shown in FIG. 7.

Since the four markers 10 are visible in the deformed state of the ring-shaped element 1 shown in FIG. 7, it can be concluded that, in this deformed state, the ring body 2 has been sufficiently deformed to create an intimate contact between the bone contact surface 4 of the ring-shaped element 1 and the bone surface 52. As such the markers 10 are suitable deformation indicators that advantageously can be used to confirm sufficient deformation of the ring body during placement of a screw element 20 in a bone of a patient.

Figure 9:
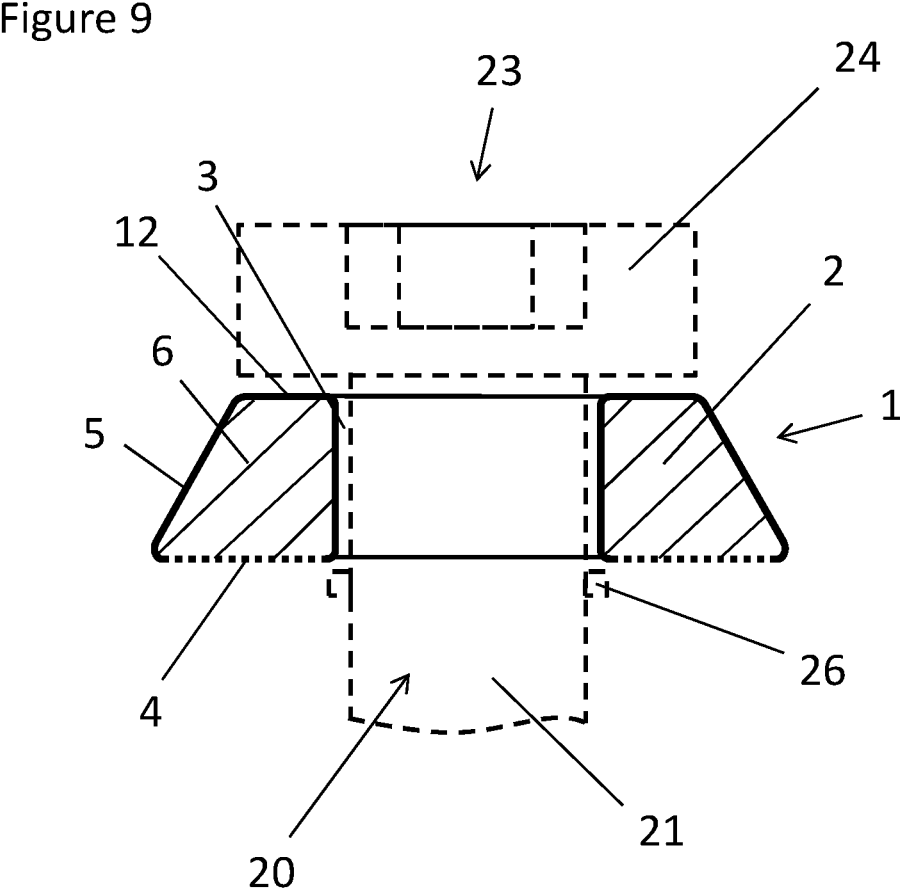
FIG. 9 shows a third alternative embodiment of a ring-shaped element according to the invention in combination with a specifically designed screw element.

FIG. 9 shows a third alternative embodiment of a combination of a ring-shaped element 1 and a surgical screw element 20. The surgical screw element 20 comprises a shank 21 and a proximal part 23 formed by screw head 24. The ring-shaped element 1 is arranged on the shank 21 of the surgical screw element 20.

The screw element 20 and the ring-shaped element 1 are specifically designed to be used in combination. The shank 21 comprises a circumferential rim 26 that is configured to hold the ring-shaped element 1 on the shank 21. The diameter of the central opening 3 of the ring-shaped element 1 is adapted to the diameter of the shank 21 and the height of the inner wall of the ring-shaped element 1 is adapted to the distance between the proximal part 23 and the circumferential rim 23.

The ring-shaped element 1 comprises a relatively small top area and a large bottom area. The top area is configured to substantially correspond with the distal surface area of the proximal part 23 so that, when the ring-shaped element 1 is squeezed between the proximal part 23 and the bone surface 52, the complete top area of the ring-shaped element 1 is pressed downwards by the proximal part 23.

The relatively large bottom area comprises the bone contact surface 4 which may therefore also be relatively large. This has the advantage that there is a relatively large surface that can be brought into contact with the bone surface 52 and through which an anaesthetic can be released to the bone surface 52.

FIG. 10 shows an alternative embodiment of a deformable body 30 according to the invention. FIG. 11 shows a cross-section B-B of the deformable body 30 of FIG. 10. The deformable body 30 comprises a bone contact surface 31 to be pressed against a bone surface of a bone, a circumferential side wall 32 and a top wall 33 opposite to the bone contact surface 31. The deformable body 30 contains an anaesthetic. The bone contact surface 31 is pervious for the anaesthetic such that, after implantation, the anaesthetic may be released through the bone contact surface 31. The circumferential side wall 32 and the top wall 33 of the deformable body 30 are not pervious for the anaesthetic such that the anaesthetic will be mainly, preferably only released through the bone contact surface 31.

The anaesthetic is arranged in the deformable body in a form that it will be released according to a predetermined controlled release profile.

The deformable body 30 is provided with four fixation locations 34 each comprising two aligned recesses 35 at opposite sides of the deformable body such that a thin part 36 is formed between each set of two recesses 35. The thin parts 36 may be pierced, for example by screw elements or separate piercing element to create through-going openings through the recesses 35. Each of these through-going openings may be used to accommodate the shank of a respective screw element to press the deformable body 30 against a bone surface. The screw elements may for example also be used to press a plate on the deformable body 30 in order to press the deformable body 30 against a bone surface. The plate may advantageously be provided with a pattern of through-going openings corresponding to the pattern of fixation locations of the deformable body 30. The plate may be provided with a lip, rim, or clip to hold the deformable body on the plate to facilitate placement of plate and deformable body 30.

It is remarked that the through-going openings created by piercing the thin parts 36 may also be used to arrange alternative fixation elements therethrough, such as wires or bands with which the bone contact surface 31 can be pressed against the bone surface in order to adapt the shape of the bone contact surface 31 to the shape of the bone surface on which the deformable body 30 is pressed. It will be clear for the man skilled in the art that many modifications may be made to adapt the deformable body, the ring-shaped element and/or the screw element to specific circumstances of the location where the deformable body and/or the combination of screw element and ring-shaped element is applied.

Figure 12:
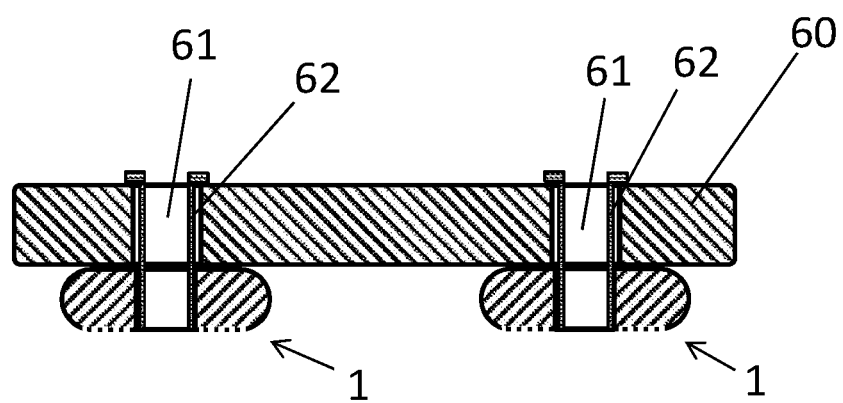
FIG. 12 shows a cross-section of a plate in combination with ring shaped elements according to an embodiment of the invention.

FIG. 12 shows a cross section of a plate element 60 with two ring-shaped elements 1 used in combination with the plate element 60. When the ring-shaped elements 1 are used in combination with the plate element 60, the ring-shaped elements 1 cannot be pre-arranged on the shank of the respective screw elements with which the plate element 60 will be mounted on a bone, since the ring-shaped elements 1 cannot be moved through the plate openings 61 provided in the plate element 60. Furthermore, it may be difficult to align a ring-shaped element 1 between the plate element 60 and an outer bone surface of a bone on which the plate element 60 is mounted once the plate element 60 is arranged in its intended location, for example when one screw element is screwed into a bone.

Therefore clips 62 are provided that hold the ring-shaped elements 1 aligned with the plate openings 61 and connected with the plate element 60, such that the ring-shaped elements 1 in combination with the plate element 60 may be arranged on a bone surface on which the plate element 60 may be mounted. The clips 62 will ensure that the ring-shaped elements 1 will remain aligned with the plate openings 61.

When a screw element 20 is arranged in the openings, the clips 62 are no longer required since the screw element 20 will keep the respective ring-shaped element 1 at the desired location, and the clips 62 may, when desired, be removed.

The clips 62 may be designed such that the clips 62 can be removed by pulling the clips 62 out of the plate openings 61 when the screw elements 20 are placed in the plate openings 61. The clips 62 may also be made of a material than can be broken or flexed by the screw element 20 such that the clips 62 do not prevent or hinder the placement of the screw element 20 through the plate openings 61 and the ring-shaped elements 1. It is also possible that the clips 62 are not removed, for example when the clips do not prevent placement of the screw element 20 and/or when the clips 62 are made of bio absorbable material.

In alternative embodiments, other means or devices may be provided to connect the ring-shaped elements 1 to the plate element 60 in an aligned position with respect to the plate openings 61. For example, the ring-shaped elements 1 may be glued to the plate element 60, or other features such as rims or bumps, matching the diameter of holes in a plate, may be provided to at least temporarily connect the ring-shaped elements 1 to the plate element 60. The ring-shaped element may also be held by clips or other elements that are not arranged in plate openings through which the fixation elements are placed but at other locations, such as other openings or an edge of the plate.

Figure 13:
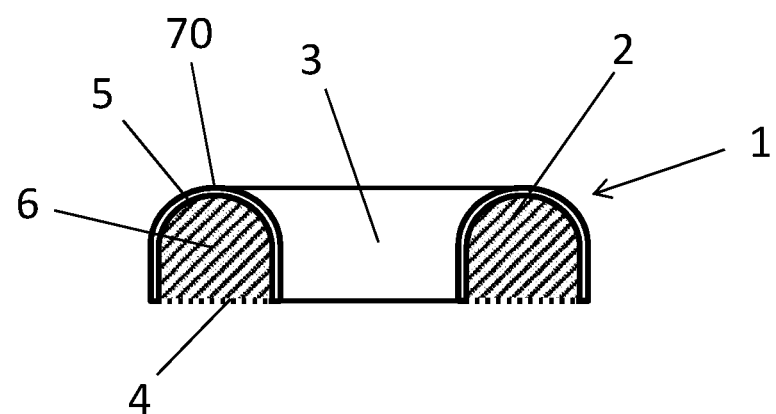
FIG. 13 shows a cross-section of a fourth alternative embodiment of a ring-shaped element according to the invention.

FIG. 13 shows a fourth alternative embodiment of a ring-shaped element according to the invention. The ring-shaped element 1 of FIG. 13 comprises an outer shell 70 that functions as the further compartment wall which is less pervious for the anaesthetic in the deformable body compared to the perviousness of the bone contact surface. The outer shell provides both mechanical robustness and directional release, i.e. release of the anaesthetic at the bone contact surface 4.

The shell 70 can be constructed from the same material as the anaesthetic containing interior of the deformable body, with altered mechanical and chemical properties, for example comprising more dense crosslinking or by an alternative method of crosslinking that results in a more stiff and non-pervious material. Alternatively, the shell 70 can be constructed from a different material, for example a polymer material. The polymer material is for example a synthetic polymer such as polylactic-co-glycolic acid (PLGA), poly-caprolactone (PCL) or polyvinyl alcohol (PVA), or a bio-polymer such as hyaluronic acid, chitosan, alginate, collagen or gelatin. These polymers can be functionalized with a variety of chemical groups to precisely modulate their characteristics.

The shell 70 provides a robust housing for the anaesthetic containing interior of the deformable body and can bear most of the mechanical strain/loads during insertion. As the permeability and porosity of the shell 70 can be adjusted, the release of the anaesthetic can be directed towards the desired location, typically the bone contact surface. This bone contact surface, with which the deformable body is placed on periosteum and bone, is not covered with the external shell 70 to provide an opportunity for diffusion of the drug and degradation of the inner part of the device.

In an alternative embodiment, the bone contact surface may be covered with the shell 70 but this part of the shell 70 has an increased porosity and permeability for the anaesthetic compared to the other parts of the external shell 70. This can be for example be achieved with macroscopic or microscopic pores. To control the ratio between anaesthetic diffusion towards the bone contact surface of the deformable body and diffusion towards the compartment wall, the porosity of the part of the shell that encapsulates the non-bone contact surfaces of the device can be adjusted via either micro- or macroscopic pores or other means of altering permeability.

The shell 70 is constructed to be flexible to adapt its shape to the bone contour on which it is implanted. The shell 70 may be biodegradable, with the degradation time ideally being similar or slightly surpassing the degradation time of the inner, drug-containing part of the device.

Figure 14:
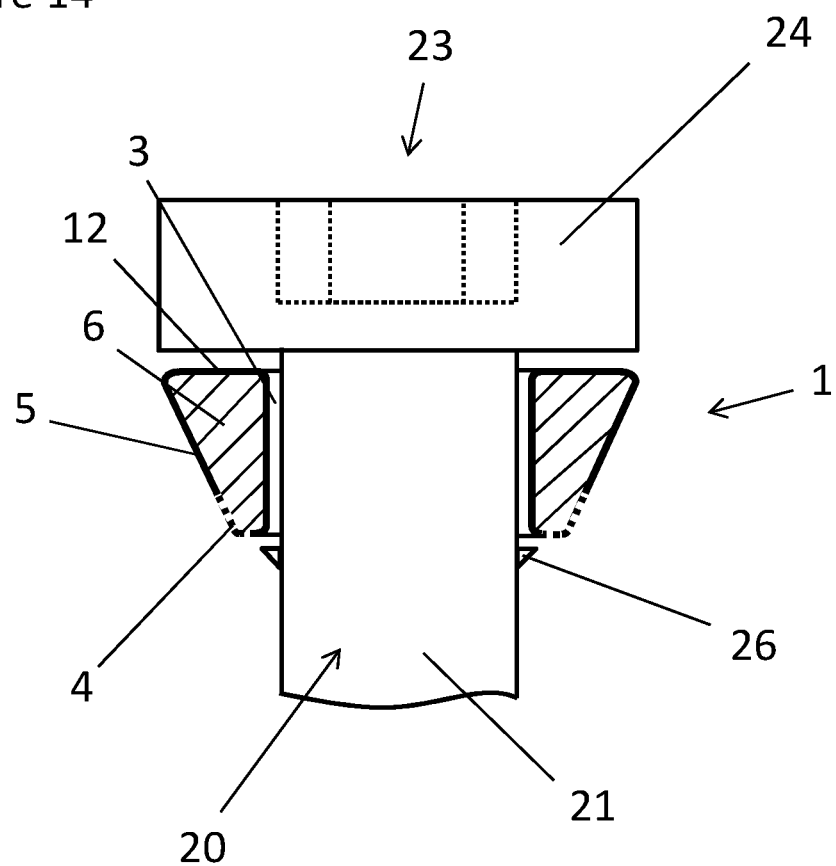
FIG. 14 shows a cross-section of a fifth alternative embodiment of a ring-shaped element according to the invention.

FIG. 14 shows an embodiment of a ring-shaped element 1 for percutaneous placement of a screw element 20 into a bone. To facilitate safe placement of deformable body and screw element 20 through the skin of a patient, the shape of the outer surface of the ring-shaped element 1 is conical wherein the diameter of the outer surface in proximal direction, i.e. away from the bone contact surface 4, increases.

Further, the maximal diameter of the ring-shaped element 1 is substantially the same as the diameter of the screw head 24. The maximum diameter of the ring-shaped element 1 may also be smaller than the diameter of the screw head 24.

The advantage of the conically increasing diameter of the outer surface of the ring-shaped element 1 and that the maximal diameter of the ring-shaped element 1 substantially corresponds with the diameter of the screw head 24 is that the ring-shaped element 1 may relatively easily be pushed through skin and underlying soft tissue until it is pressed against the periosteum of the bone in which the screw element 20 is placed. Thereby, there is less risk of damaging the ring-shaped element 1.

To protect the material of the ring-shaped element 1, the material of the deformable body may, at least partially, for example the outer surface, be made relatively strong.

Figure 15:
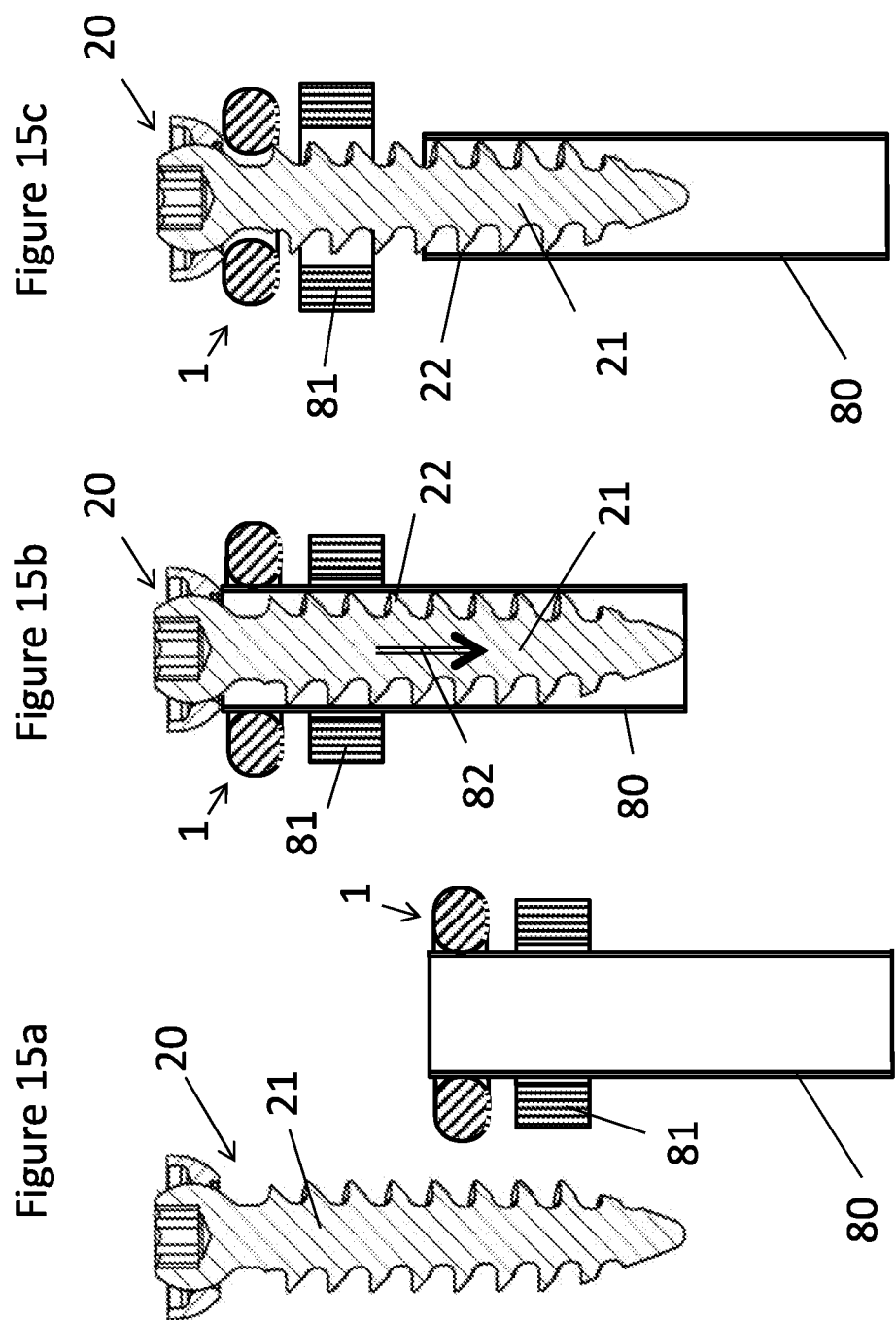
FIGS. 15a, 15b and 15c show a method to arrange a ring-shaped element on a shank of a screw element as shown in FIG. 3.

FIGS. 15*a*, 15*b* and 15*c* show a method to mount a ring-shaped element 1 on a shank 21 of a screw element 20. The method provides a relatively easy and reliable manner to arrange the ring-shaped element 1 on a screw element 20.

The method may also protect the relatively soft material of the ring-shaped element 1, and does not require direct manual contact with the hands of a person handling the ring shaped-element 1.

In FIG. 15a, the ring-shaped element 1 is shown before being mounted on the shank 21 of the screw element 20. The ring-shaped element 1 is arranged on one end of a sleeve 80. The sleeve 80 may be made of relatively strong material that is not easily damaged by the screw thread 22. The ring-shaped element 1 may be arranged during production on the sleeve 80 or this may be done just for mounting of the ring-shaped element 1 on the screw element 20. When the ring-shaped element 1 is arranged on the sleeve 80, the sleeve will also facilitate placement of the ring-shaped element 1 in the correct orientation on the screw element 20, i.e. with the bone contact surface 4 facing the distal end of the screw element 20.

On the sleeve 80, a pusher element 81 is arranged. The pusher element 81 is provided to push, as explained hereinafter, the ring-shaped element 1 from the sleeve 80. The pusher element 81 can slide over the outer surface of the sleeve 80.

In FIG. 15b, the screw element 20 is moved into the sleeve 80, as indicated by arrow 82. The ring-shaped element 1 is now properly aligned with the location where the ring-shaped element 1 should be arranged on the shank 21 of the screw element 20. Since the shank 21 and its screw thread 22 are moved through the interior of the sleeve 80, the ring-shaped element 1, which is arranged on the outer surface of the sleeve 80 cannot be damaged by the screw thread.

From the position in FIG. 15b, the sleeve 80 can be pulled from the shank 21 of the screw element 20, while the ring-shaped element 1 is held in its relative position with respect to the screw element 20, for example by pushing the pusher element 81 against the ring-shaped element 1. As a result, the pusher element 81 will push the ring-shaped element 1 from the sleeve into the position shown in FIG. 15c. Once the ring-shaped element 1 is arranged in its desired position with respect to the shank 21 of the screw element 20, as shown in FIG. 15c, the sleeve 80 and the pusher element 81 may be removed from the shank 21.

The sleeve 80 shown in FIGS. 15a, 15b and 15c is a stiff sleeve. In an alternative embodiment, the sleeve may be more flexible.

Before use, the ring-shaped element 1 and the sleeve 80 may be connected to each other, for example by a tear line or cut line that is torn or cut after the ring-shaped element 1 is arranged at the desired location on the shank 21 of the screw element 20. The tear line or cut line may be provided between the ring-shaped element 1 and the sleeve 80, or in the sleeve 80 itself.

In another embodiment of the ring-shaped element, the inner surface of the ring-shaped element, i.e. the surface facing towards the longitudinal axis may be provided with a layer of relatively strong material, such as for example shown in FIG. 14, to protect the ring-shaped element 1 when it is moved over the shank 21 of the screw element 20.

Figure 16:
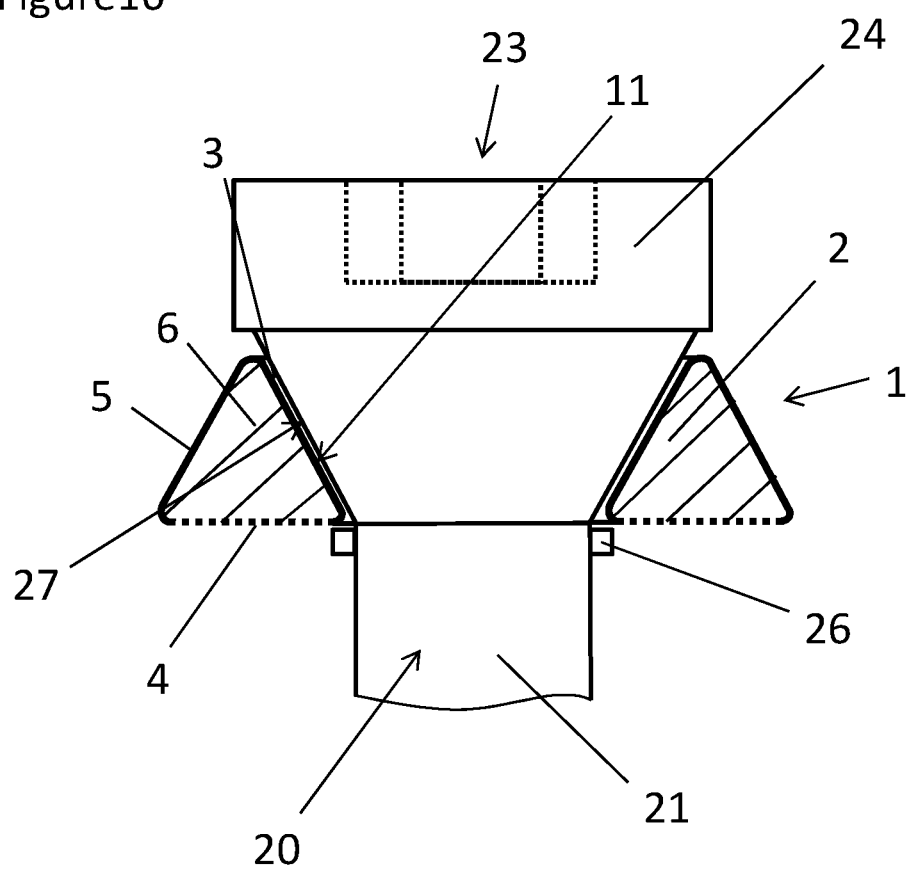
FIG. 16 shows a further combination of a screw element and a ring-shaped element according to an embodiment of the invention.

FIG. 16 shows an embodiment of a ring-shaped element 1 in combination with a screw element 20. The screw element 20 comprises a conical shank part 27 having a conical outer surface 28 mating with a conical inner surface 11 of the ring-shaped element 1. The angle of conical outer surface 28 and the conical inner surface with respect to the longitudinal axis of the screw element 20 and the ring-shaped element 1 are substantially the same. When the screw element 20 is screwed into a bone and the bone contact surface will be pushed against the periosteum of the bone, the ring will not only be pressed in axial direction but also in radial direction. This may have the advantage that the ring-shaped element 1 may be applied over a larger insertion range of the screw element 20 without exerting a too large, radially-directed, force on the material of the ring-shaped element 1.

The invention claimed is:

1. A deformable body,
   wherein the deformable body comprises a bone contact surface to be placed on periosteum of a bone surface of a bone such that the bone contact surface adapts its shape to the shape of the bone surface,
   wherein the deformable body comprises one or more through-going openings arranged to receive a fixation element, and
   wherein the deformable body comprises a pharmaceutical or biological compound that is released from or through the bone contact surface according to a release profile.

2. The deformable body of claim 1, wherein the deformable body is a ring shaped body having an opening being one of the one or more through-going openings and through which a shank of a surgical screw element can be placed, wherein the bone contact surface is to be pressed against bone surface by screwing of the screw element in a bone while the deformable body is placed on the shank of the screw element.

3. The deformable body of claim 1, wherein the bone contact surface is pervious for the pharmaceutical or biological compound to be released.

4. The deformable body of claim 1, wherein the pharmaceutical or biological compound is arranged in a compartment delimited by the bone contact surface and a further compartment wall, wherein the further compartment wall is a substantially non-pervious wall for the pharmaceutical or biological compound such that the pharmaceutical or biological compound will mainly be released through the bone contact surface.

5. The deformable body of claim 4, wherein the further compartment wall is an outer wall of the deformable body.

6. The deformable body of claim 1, wherein the pharmaceutical or biological compound is arranged in a compartment delimited by the bone contact surface and a further compartment wall, wherein the bone contact surface has a first release rate for the pharmaceutical or biological compound to be released and wherein the further compartment wall has a second release rate for the pharmaceutical or biological compound to be released, wherein the first release rate is larger than the second release rate.

7. The deformable body of claim 1, wherein the deformable body comprises a second compartment at least partially delimited by a release surface, wherein the second compartment comprises a second pharmaceutical or biological compound, and wherein the release surface is pervious for the second pharmaceutical or biological compound.

8. The deformable body of claim 1, wherein the deformable body comprises one or more deformation indicators that indicate a deformation of the deformable body.

9. The deformable body of claim 1, wherein the anaesthetic is only or mainly released from or through the bone contact surface.

10. The deformable body of claim 1, wherein the anaesthetic comprises bupivacaine, liposome bupivacaine, lidocaine and/or levobupivacaine.

11. The deformable body of claim 1, wherein the deformable body comprises one or more indicators indicating a location of the bone contact surface.

12. The deformable body of claim 1, wherein the deformable body is made of a visco-elastic material, a degradable felt material, a sponge-like material, a gelatin material, a gel, in particular a hydrogel, a polymer or any combination thereof.

13. The deformable body of claim 1, wherein the deformable body comprises a force application surface to apply a force on the deformable body, wherein the bone contact surface is arranged at a first side of the deformable body and the force application surface is arranged at a second side of the deformable body, wherein the first side and the second side are opposite sides of the deformable body.

14. A combination of the deformable body of claim 1 and a surgical screw element having a shank, wherein the shank of the surgical screw element extends through one of the one or more through-going openings.

15. The combination of claim 14, wherein the shank comprises a circumferential rim or circumferential detention that mates with the deformable body to hold deformable body on the shank.

16. The combination of claim 14, wherein the screw element is a pedicle screw for spinal treatment.

17. A kit comprising:
the combination of claim 14 having an opening
a sleeve, wherein the sleeve can be arranged in the opening and wherein the sleeve comprises a channel to receive the shank of a surgical screw element, and
wherein the sleeve is arranged to be slid over the shank of a screw element to position the deformable body on a desired position on the shank.

18. The kit of claim 17, wherein the kit further comprises a pusher element to push the deformable body from the sleeve.

19. Bupivicaine, liposome bupivacaine, lidocaine or levobupivacaine for use in a method of treating pain, in particular pain caused by placing a surgical screw element through periosteum of a bone of a patient,
wherein the bupivacaine, liposome bupivacaine, lidocaine or levobupivacaine is administered by the deformable body of claim 1.

20. The deformable body of claim 1, wherein the pharmaceutical or biological compound comprises anaesthetics, antibiotics, bone growth stimulating agents, analgesics, chemotherapeutic agents, steroids, including retinoids, hormones, anti-microbials, antivirals, anti-inflammatory compounds, radiation absorbers, including UV-absorbers, vaccins, and/or stemcells.

21. A method of treating pain, in particular pain caused by placing a surgical screw element through periosteum of a bone of a patient, comprising the steps of:
placing a deformable body on a shank of the surgical screw element, wherein the deformable body comprises a bone contact surface to be pressed against bone surface upon screwing of the screw element in a bone, and wherein the deformable body comprises a pharmaceutical or biological compound that is released from or through the bone contact surface,
screwing the surgical screw element into the bone of the patient, whereby the deformable body is squeezed between the bone surface and a proximal part of the screw element to press the bone contact surface against bone surface, and
releasing the pharmaceutical or biological compound from or through the bone contact surface.

* * * * *